United States Patent [19]

Avron et al.

[11] 4,199,895

[45] Apr. 29, 1980

[54] PRODUCTION OF GLYCEROL, CAROTENES AND ALGAE MEAL

[75] Inventors: Mordhay Avron, Rehovot; Ami Ben-Amotz, Ramat Gan, both of Israel

[73] Assignee: Yeda Research and Development Co. Ltd., Rehovot, Israel

[21] Appl. No.: 918,802

[22] Filed: Jun. 26, 1978

Related U.S. Application Data

[63] Continuation-in-part of Ser. No. 800,521, May 25, 1977, Pat. No. 4,115,949.

[30] Foreign Application Priority Data

Jun. 9, 1978 [IL] Israel ............................. 54881

[51] Int. Cl.$^2$ .............................................. A01G 7/00
[52] U.S. Cl. ............................................... 47/1.4
[58] Field of Search ..................................... 47/1.4

[56] References Cited

U.S. PATENT DOCUMENTS

| | | | |
|---|---|---|---|
| 2,732,661 | 1/1956 | Spoehr et al. | 47/1.4 |
| 2,732,662 | 1/1956 | Myers et al. | 47/1.4 |
| 2,949,700 | 8/1960 | Kathrein | 47/1.4 |
| 3,403,471 | 10/1968 | Clement et al. | 47/1.4 |
| 3,650,068 | 3/1972 | Meyer et al. | 47/1.4 |
| 4,115,949 | 9/1978 | Avron et al. | 47/1.4 |

FOREIGN PATENT DOCUMENTS 486999   2/1976   Australia ............................. 47/1.4

OTHER PUBLICATIONS

An Extreme Source of Carotene, Aasen et al., 1969, Acta. Chem. Scand. 23, 2544–2545.
The Role of Glycerol —, Ben–Amotz et al., 1973, Plant Physiol. 51, 875–878.
The Salt Relations —, Borowitzka et al., 1974, Arch. Microbiol. 96, 37–52.
Physiological Aspects of Salt —, Borowitzka, 1974, Thesis, School of Microbiology, Univ. of New South Wales, N.S.W.

*Primary Examiner*—Robert E. Bagwill
*Attorney, Agent, or Firm*—Browdy and Neimark

[57] ABSTRACT

According to the invention there is provided a process for the simultaneous production of glycerol, carotenes($\beta$-carotene, its isomers and carotene-like substances) and protein rich material which comprises cultivating algae of the *Dunaliella bardawil* species under high-intensity illumination in a growth medium containing a high concentration of sodium chloride (at least 1,5 M in the final stage of the cultivation), providing an adequate supply of carbon, in a depth of not exceeding 20 cm of the aqueous medium, in a diurnal cycle of illumination, until algae of high content of the above three components are obtained, harvesting the algae and recovering from same the three constituents.

11 Claims, No Drawings

PRODUCTION OF GLYCEROL, CAROTENES AND ALGAE MEAL

RELATION WITH PRIOR APPLICATION

The present patent application is a Continuation-in-Part or prior patent application No. 800,521, filed on May 25, 1977 now U.S. Pat. No. 4,115,949.

FIELD OF THE INVENTION

A process for the simultaneous production of glycerol, of β-carotene and its isomers in high yields and of high-protein food by cultivation and working up of a certain type of alga is provided, and conditions of cultivation and working up are defined. The products obtained are of value: glycerol can be used as intermediate in the production of various chemicals and also as source of energy; carotenes are of value as coloring materials which are safe as they are natural products, and can be used as substances having vitamin A activity.

STATE OF THE PRIOR ART

The fact that glycerol is contained in algae of the genus Dunaliella is known, and it is also known that the content of glycerol is a function of an equilibrium established between the algae and the environment in which they are grown, i.e. the sodium chloride content of the growth medium. The relationship between glycerol content and sodium chloride content of the environment has been described in Plant Physiology (1973) 51, 875–878 in which it was shown that as about 1.5 M NaCl content of the medium on intracellular glycerol content of about 2.1 M was established.

It is also known that some of the genus Dunaliella algae have a content of carotenes and carotene like substances, and that these impart to such algae a reddish-brown color. The content of carotenes is generally quite low and generally does not exceed about 1% by weight.

SUMMARY OF THE INVENTION

A species of alga has been isolated and cultivated as a pure algal culture, which can be used for the production of glycerol and carotenes in high quantities, and a residue which has a high protein content and which can be used as feed supplement for animal feedstuffs and for similar purposes.

In the following the carotenes and carotene like substances which are contained in the algae and which are recovered from same in pure and crystalline form are defined as "carotene". This is actually a mixture comprising mainly β-carotene and its isomers, and similar substances. This substance is of value as vitamin and as food-color. It is known that such substances are widely used for coloring various edibles, and especially margarine, soft drinks and similar products where the yellowish color is of importance and appeals to the buyer.

The present invention provides a process for the controlled cultivation of a novel type of algae, designated by us as *Dunaliella bardawil* (ATCC 30861), which belongs to the Class of Chlorophycae, Order of Volvocales and which was deposited by us in the University of Texas International Culture Collection of Algae, Austin 78712, USA.

The algae used in the process of the present invention are unicellular motile cells of about 15 to 19 μm long and 10 to 14 μm in diameter, which are broadly ovoid or ellipsoid in shape with a fine elastic periplast but with no rigid cell wall. Two flagella 1.5 to 2 times the length of the cell emerge from one edge of the long cell axis, one large chloroplast occupies about half the cell volume and is often arranged in a cup-shape around the nucleus. A single median pyrenoid is embedded in the basal portion of the chloroplast and surrounded by starch granules. The cell volume is 200 to 1000 μm$^3$. The cells reproduce vegetatively by longitudinal division of the motile cells. After extensive experiments optimum conditions of cultivation have been defined which result in the desired simultaneous production of large quantities of both glycerol and of carotene, providing as byproduct a substance having a high protein content and which can be utilized for various purposes.

When grown outdoors under suitably strong illumination the cells are bright orange and have a high carotene content, which can reach values as high as 50 to 90 mg per gram dry weight of algae. When cultivated under suitable conditions the glycerol content can attain values as high as 300 to 400 mg per gram dry weight of algae.

The algae must be cultivated under an adequately high intensity of illumination, and this is best carried out outdoors in sunlight. If artificial light is used, the intensity of illumination ought to be at least about 1500 f.c. When cultivated outdoors the depth of the water ought not to exceed about 15 cm, and the optimum is about 5 cm.

In the following the content of glycerol, carotene, chlorophyll and protein of algae are specified, both when grown outdoors and under artificial illumination.

CONTENT OF GLYCEROL, β-CAROTENE AND ITS ISOMERS UNDER FAVORABLE CONDITIONS

|  | Growth outdoors, 3 M NaCl | Growth indoors, 3 M NaCl |
| --- | --- | --- |
| Chlorophyll pg/cell | 4–8 | 10–16 |
| β carotene pg/cell | 50–90 | 8–16 |
| Glycerol pg/cell | 300–400 | 200–275 |
| Chlorophyll mg/g dry wt. | 8–12 | 13–21 |
| Carotene mg/g dry wt. | 50–90 | 10–21 |
| Glycerol mg/g dry wt. | 300–400 | 270–370 |
| Protein mg/g dry wt. | 300–400 | 300–400 |

The cultivation is carried out either on an artificial medium or on sea-water adjusted so as to contain the required nutrients and salt concentration.

An artificial medium ought to contain the following nutrients:

NaCl, 1–5 M, and preferably 3–4 M; Mg$^{++}$, 1–500 mM, and preferably 5 mM; K$^+$, 1–10 mM; Ca$^{++}$, 0.1–20 mM and preferably 0.2–0.4 mM; iron source, such as Fe-EDTA 0.5–45 μM, and preferably 1–2 μM; SO$_4^{--}$, 1–5 mM; Nitrogen source, as NO$_3^-$, 1–20 mM and preferably 3–4 mM, or NH$_4$NO$_3$ 0.5–2.5 mM and preferably 1–2 mM; phosphate, 0.01–1 mM.

It is possible to use seawater augmented by addition of various constituents or concentrated by partial evaporation and addition of certain constituents. This ought to have a sodium chloride content of up to 1–4.5 M NaCl and preferably 3 M NaCl supplemented with a nitrogen source such as NH$_4$NO$_3$, 0.5–2.5 mM, and preferably 1–2 mM, phosphate source such as KH$_2$PO$_4$ 0.01–1 mM, and preferably 0.1 mM, and an iron source such as FeCl$_3$-EDTA, 0.5–50 μM preferably 2 μM.

There must be provided a suitable and adequate source of carbon, such as 10 mM NaHCO$_3$ or CO$_2$ at about 300 liter CO$_2$ per m$^3$ growth medium per day. When CO$_2$ is used as the carbon source, it is added by demand via a pH controlled solenoid valve. Other inorganic carbon sources such as CaCO$_3$, organic carbon sources such as sewage water, etc., are also suitable for growth.

The optimum pH for cultivation is between pH 7.0 and pH 9.0 and this is advantageously adjusted by adding required quantities of carbon dioxide, mineral acids such as hydrochloric acid or nitric acid, via a pH controlled valve.

The optimum temperature of cultivation is in the range of about 25°–35°, and the algae withstand temperatures of about 4° C. to 40° C.

Various contaminant microorganisms, such as fungi, zooplankton, crustaceae etc. constitute a problem under conditions of large-scale cultivation and this can be overcome to a very large extent by carrying out the cultivation at a sodium chloride concentration of above about 3.0 M. The content of glycerol increases with the concentration of the sodium chloride in the growth medium. It is desirable to effect cultivation around 3.0 M NaCl.

In order to obtain a high content of carotene it is necessary to provide adequate intensity of illumination, as pointed out above. It is further necessary to supply a limiting concentration of nitrogen which can be provided in the form of nitrate such as potassium nitrate, sodium nitrate, ammonium nitrate or by ammonia. When cultivation is carried out at a high sodium chloride content and under strong illumination the nitrogen content ought to be below 4 mM; when cultivation is effected under lesser intensities of illumination and at a smaller sodium chloride concentration, the nitrogen content ought not to exceed about 1 mM for optimum carotene content. A diurnal cycle ought to be maintained as under constant intense illumination severe inhibition of growth takes place.

The rate of reproduction of the algae is higher when the concentration of sodium chloride is not too high. The rate at about 1.5 M is about twice that at 4 M NaCl. In view of this it is possible to carry out a first step of cultivation at a lower sodium chloride concentration and to transfer the algae to a culture medium having a higher content of sodium chloride or to increase the NaCl content of the medium.

The algae are quite large and heavy, especially when the cultivation is terminated at a high sodium chloride content and in view of this it is easy to harvest the algae by sedimentation.

The glycerol and carotene can be recovered from the algae and there remains a residue having a high protein content. The amino acid composition of the algae and of the algae meal remaining after solvent extraction is as follows:

| Amino acid: | Amino Acids Analysis of *Dunaliella bardawil* | |
|---|---|---|
| | Dried algae pellet (40% protein) g/100 g protein | Dry material after solvent extraction (70% protein) g/100 g protein |
| Alanine | 7.5 | 6.8 |
| Arginine | 7.3 | 7.5 |
| Aspartic acid | 10.6 | 10.6 |
| Cysteine | 1.2 | 1.3 |
| Glutamic acid | 12.9 | 12.6 |
| Glycine | 5.7 | 5.9 |
| Histidine | 1.8 | 1.7 |
| Isoleucine | 4.2 | 4.0 |
| Leucine | 11.0 | 11.1 |
| Lysine | 7.0 | 7.6 |
| Methionine | 2.3 | 1.7 |
| Phenylalanine | 5.8 | 5.7 |
| Proline | 3.3 | 2.8 |
| Serine | 4.7 | 4.9 |
| Threonine | 5.4 | 5.5 |
| Tryptophane | 0.7 | 0.4 |
| Tyrosine | 3.7 | 3.9 |
| Valine | 5.8 | 5.7 |

The algae are harvested and the recovery of the glycerol and of the carotene can be effected by two different routes:

a. The algae are dried, disintegrated by mechanical means such as milling, carotene is extracted by means of a small amount of a polar solvent in a non-polar medium (for example 3% ethonal in hexane), the proteinous cake which contains glycerol is extracted with ethanol; the ethanol is recovered and the glycerol is decolorized and distilled to obtain it in purified form, bleached and evaporated, giving pure glycerol. The proteinous meal is dried and can be used as algae meal for known purposes. The solvent can be recovered from the carotene extract; the carotene is purified by chromatography and obtained in crystalline form.

b. The algae are suspended in aqueous ethanol, the proteinous cake containing the carotene is separated, carotene is extracted by means of non-polar organic solvents such as hexane, cyclohexane or benzene, the solvent is recovered and the carotene is purified and crystallized. The chlorophyll is removed from the ethanolic glycerol solution, the alcohol is recovered and the glycerol is decolorized and refined by distillation to give an essentially pure product. The proteinous meal is dried and can be used as such.

The novel process of cultivation under controlled conditions on a predetermined culture medium provides the possibility to obtain simultaneously three valuable products: glycerol, carotenes and algae meal. The high glycerol content (30 to 40%) and the high carotene content (above 2%, and under favorable conditions up to about 5 percent by weight under large-scale cultivation conditions) is a substantial improvement over processes used hitherto.

EXAMPLE 1

Cultivation of *Dunallella bardawll* for Glycerol and Carotene Production.

*D. bardawil* was grown in a seawater medium containing 3 M NaCl, supplemented with 2 mM NH$_4$NO$_3$, 0.2 mM KH$_2$PO$_4$, 2 μM FeCl$_3$ and 20 μM EDTA. CO$_2$, as carbon source was added by demand via a pH controlled solenoid valve at about 300 liters CO$_2$ per m$^3$ growth medium per day. The pH is maintained automatically at pH 7.8–8.2 by adding CO$_2$ on demand. The algae were grown outdoors in a 10 cm deep open pond under natural conditions of solar irradiation and temperature. The culture was mixed by continuous flow in a canal of about 1 meter width at a flow rate of about 10 cm/sec. A low head high volume centrifugal pump made the culture flow. $CO_2$ was introduced at a controlled rate by the outlet of the pump.

*D. bardawil* grew at a rate of 0.5–1.0 division per day and was harvested when the cells contained 200 mg glycerol per liter medium.

Cultures were harvested by continuous centrifugation in a Westphalia separator model SA-1 (Clarifier model) with a flow rate of 350 liters per hours. About half of the culture was harvested each day with the remaining culture diluted accordingly with the clear supernatant and the necessary nutrients, to maintain the concentrations indicated.

The product of centrifugation, wet algal paste (48% dry weight), was drum dried glycerol and carotene were extracted and obtained in a pure form as set out above.

| Products: | |
|---|---|
| Dried algae, containing glycerol, protein and carotene | $30 gr/m^2 \times day$ |
| Glycerol | $10 gr/m^2 \times day$ |
| Carotene | $0.7 gr/m^2 \times day$ |

EXAMPLE 2

Production of high carotene content algae

*Dunaliella bardawil* was cultivated as in Example No. 1, but with depth of the growth medium of 5 cm and harvesting at a glycerol concentration of 100 mg/liter.

PRODUCTIVITY

| Products: | |
|---|---|
| Dried algae | $8 gr/m^2 \times day$ |
| Glycerol | $2.5 gr/m^2 \times day$ |
| Carotene | $0.6 gr/m^2 \times day$ |

EXAMPLE 3

Production of Carotene and Glycerol.

Cultivation was the same as in Example No. 1, but at a NaCl concentration of 4.5 M and in water body 5 cm deep. The division rate under these conditions is 0.5/day. The algae were harvested at a glycerol concentration of 200 mg/liter.

| Products: | |
|---|---|
| Dried algae: | $8.2 gr/m^2 \times day$ |
| Glycerol: | $3.3 gr/m^2 \times day$ |

| -continued | |
|---|---|
| Products: | |
| Carotene: | $0.8 gr/m^2 \times day$ |

We claim:

1. A process for the simultaneous production of glycerol, carotenes and protein-rich material which comprises cultivating algae of the *Dunaliella bardawil* species under high-intensity illumination in a growth medium containing an amount sufficient of nutrients including nitrogen to effect growth of said algae and a high concentration of sodium chloride which reaches at least 1.5 M in the final stage of the cultivation, providing an adequate supply of carbon, in a depth of not exceeding 20 cm of the aqueous medium, in a diurnal cycle of illumination, until algae of high content of the above three components are obtained, harvesting the algae and recovering from same the three constituents.

2. A process according to claim 1, wherein said growth medium is an artificial growth medium containing:

NaCl, 1–5 M; $Mg^{++}$, 1–500 mM; $K^+$, 1–10 mM; $Ca^{++}$, 0.1–20 mM; iron source, 0.5–45 μM; $SO_4^{--}$, 1–5 mM; nitrogen source, as $NO_3^-$, 1–20 mM, or $NH_4NO_3$ 0.5–2.5 mM; phosphate, 0.01–1 mM.

3. A process according to claim 1, wherein the cultivation is carried out in sunlight.

4. A process according to claim 1, wherein the carbon is supplied in the form of carbon dioxide or in the form of a carbonate or bicarbonate at a pH of from 7.0 to 9.0.

5. A process according to claim 1, wherein the cultivation is effected in a medium containing sodium chloride in a concentration from a 3 M to saturation concentration.

6. A process according to claim 1, wherein the algae are harvested by sedimentation.

7. A process according to claim 1, wherein the glycerol is extracted by means of an organic solvent which is recovered, and which glycerol is purified by decolorization and subsequent distillation.

8. A process according to claim 7 wherein the organic solvent is an alcohol.

9. A process according to claim 1, wherein the carotene is extracted by means of a small amount of a polar solvent in an apolar solvent, the solvents are recovered and the carotenes are purified and crystallized.

10. A process according to claim 8 wherein the polar solvent is ethanol and the apolar solvent is hexane.

11. A process according to claim 1 wherein the algae are grown on a medium of above 3 M sodium chloride, under sunlight illumination, in a diurnal cycle, on a medium containing below 4 mM nitrogen on a medium providing the nutritive requirements, until a glycerol content of at least 25% and at least 3% carotenes calculated on dry weight of algae cells is established, harvesting the algae and recovering from same the 3 products: glycerol, carotenes and algae meal.

* * * * *